(12) United States Patent  
Loppacher et al.

(10) Patent No.: US 9,465,017 B2  
(45) Date of Patent: Oct. 11, 2016

(54) METHOD AND DEVICE FOR PREPARING SUBSTANCES FOR QUALITATIVE AND QUANTITATIVE ANALYSES

(75) Inventors: Matthias Loppacher, Basel (CH); Eike Reich, Rheinfelden (CH)

(73) Assignee: CAMAG, Muttenz (CH)

( * ) Notice: Subject to any disclaimer, the term of this patent is extended or adjusted under 35 U.S.C. 154(b) by 560 days.

(21) Appl. No.: 13/386,034

(22) PCT Filed: Jul. 16, 2010

(86) PCT No.: PCT/IB2010/053262  
§ 371 (c)(1),  
(2), (4) Date: Jan. 20, 2012

(87) PCT Pub. No.: WO2011/010265  
PCT Pub. Date: Jan. 27, 2011

(65) Prior Publication Data  
US 2012/0125127 A1    May 24, 2012

(30) Foreign Application Priority Data

Jul. 24, 2009   (CH) ..................................... 1166/09

(51) Int. Cl.  
*G01N 1/02*    (2006.01)  
*G01N 30/90*   (2006.01)  
*G01N 35/10*   (2006.01)  
*G01N 1/40*    (2006.01)  
*G01N 30/00*   (2006.01)

(52) U.S. Cl.  
CPC .......... *G01N 30/90* (2013.01); *G01N 35/1095* (2013.01); *G01N 2001/4061* (2013.01); *G01N 2030/009* (2013.01)

(58) Field of Classification Search  
None  
See application file for complete search history.

(56) References Cited

U.S. PATENT DOCUMENTS

| | | | |
|---|---|---|---|
| 4,722,830 A * | 2/1988 | Urie et al. ...................... 422/62 |
| 5,783,938 A * | 7/1998 | Munson et al. ............. 324/71.2 |
| 6,872,361 B2* | 3/2005 | Li et al. ........................ 422/540 |
| 7,354,775 B2* | 4/2008 | Yoshida et al. .............. 436/522 |
| 2012/0190589 A1* | 7/2012 | Anderson et al. ............. 506/39 |

* cited by examiner

*Primary Examiner* — Robert R Raevis  
(74) *Attorney, Agent, or Firm* — Buchanan Ingersoll & Rooney PC

(57) ABSTRACT

A method and a device for preparing a qualitative and quantitative analysis of samples are presented. The device affords the possibility of delimiting and isolating a specific region of a solid or liquid sample. A liquid, e.g. a solvent or extracting agent, is added in the delimited and isolated region. Thereafter the created mixture of substance and liquid is, in a plug-shaped fashion, pressed out of the closed region by means of a neutral liquid or the same liquid, and supplied to the measuring instrument in the form of a highly concentrated solution.

10 Claims, 9 Drawing Sheets

METHOD AND DEVICE FOR PREPARING SUBSTANCES FOR QUALITATIVE AND QUANTITATIVE ANALYSES

The present invention relates to a method and device for preparing substances for qualitative and quantitative analyses.

Currently there are no simple methods for providing very precise measurement values in analysis using small amounts of substance samples, for example biologically active samples such as e.g. samples of blood, bone marrow, cerebrospinal and synovial fluids, sperm, stool etc., which are taken for subsequent analysis in the laboratory. The available methods for dried (drop) samples of e.g. blood or urine in particular, or for other dried biological samples, are complicated, take a lot of time and are too rudimentary for some analyses to ensure precise and reliable data. In order to transport the samples and supply them to the measuring instruments in e.g. test tubes, said samples must normally be available in solution, emulsion or in diluted mixture form. Such samples contain relatively small proportions of the sought-after substances to be evaluated. It would be desirable, particularly in drugs screenings or drugs tests, but also in any other routine examination, for only the desired substances to be available in the highest-possible concentration for the measurement so as to be able to carry out precise measurements in a short period of time.

It would be desirable to remove the substance from the matrix of the sample using a known method. However, since there is usually only a small amount of the sample and the substances are often only contained therein in very small quantities and can therefore not be fed to a measuring instrument without carrier liquid, one makes do with combining the substances with known liquids and media such as e.g. methanol or buffer solutions as carrier that do not cause interference in the measuring instrument. In the context of the measurement in the analysis instrument, many parts of the sample should be referred to as ballast; they prevent a precise measurement. The relative proportion of the analyte (part of the specimen to be tested) increases as the amount of such a ballast, which is typically a matrix of the sample in the specimen, extract or solution to be examined, decreases. Now, if this analyte, together with a known amount of one of its isotopes, constitutes a mixture that makes up a large proportion of the specimen, there is a high chance of a precise measurement.

The present method and the device presented here are based on findings obtained from the methods in thin-layer chromatography. DE10036293A1 by Luftmann describes a device that can be used to isolate samples. U.S. Pat. No. 5,208,458 by Busch presents a method and a device with the aid of which defined samples can be taken from gel. However, it was found that Busch's idea, on which his patent is based, cannot be implemented in practice in the application for gel.

The present invention is now based on the object of improving the method and device for preparing substances for qualitative and quantitative analyses, of the type mentioned at the outset, of samples and microscopic sections which are liquid, highly viscous, dried, coagulated or thickened, are present in solid form, are biologically active dried or have had protective colloids added for stabilization such that the substances can be supplied highly concentrated to the known analysis methods and instruments and in defined surroundings. This also allows small amounts of the substances to be examined to be analyzed reliably and precisely in highly-concentrated form.

In a sample the sought-after substance is generally embedded in a matrix. This matrix may consist of insolubly solid or soluble components. The goal of the presented method is to "wash out" the sought-after substance—the analyte—from the samples and to supply it to the measuring instrument as a specimen together with a dragged-along or dissolved matrix, the added liquid and possibly an internal standard. Depending on the composition of the sample, this is brought about by simple washing out, solubilizing or extracting. Here, the substance is dissolved out of the matrix such that it can be supplied to the measuring instrument, e.g. the spectrometer, together with the liquid, e.g. a solvent or an extracting agent. The more directly (short line) a specimen reaches the measuring point in this state and the higher the concentration thereof is, the more reliable the measurement becomes.

The first step of the method consists of isolating and enclosing a defined region of the sample from the surroundings in a cavity 3 (FIG. 1) using the instrument described below. Here, the sealing edges 4 and 5 provide the most important part of the seal. However, it is also possible to squish (FIG. 2) material of the samples 11 between the sealing edges 4, 5 in order to achieve improved sealing.

In a further step, an amount of liquid that is as small as possible but sufficient is thereupon added to the now closed-off space and said liquid comes into contact with the sample in the closed cavity 3. Depending on the property of the sample and the substance contained therein, this liquid can either be used for direct rinsing, dissolving or extracting, or a soaking process must precede the rinsing. In the latter case, the liquid is, in a next step, kept together with the sample for a certain amount of time in the closed region together with the sample, and only rinsed out as a specimen after this. The time required for soaking depends on the properties of the sample, the liquid and the substance, but is usually in the region of 1-60 seconds.

Whether it is possible to perform direct washing out or whether a dissolving or extraction process needs to be initiated is likewise dependent on the type of sample, the supplied liquid and the substance. The presented method permits all options. For each substance, laboratory trials set the type and amount of liquid that needs to be supplied and what process is necessary for preparing the substance such that it subsequently is transportable in a liquid state and allows the measurement of precise analysis values.

The goal of the preceding steps is to supply a highly concentrated fraction of the substance to the measuring instrument via the discharge line 9, which substance is dissolved together in the clearly defined liquid or mixed with the same. Here, this is referred to as a "specimen". It is desirable to "take along" to the measuring instrument as few interfering parts of the matrix as possible. In order to prevent the specimen from having too much of the supplied liquid, the mixture of the extracted or dissolved substance is pressed out of the isolated cavity 3 in a plug-shaped fashion and supplied to the line to the measuring instrument. What is important here is that the paths are short and the substance is brought to the measuring site in the most direct fashion.

The required number of, time for and sequence of the method steps may vary greatly depending on the sample and the matrix thereof. As described above, these are set and defined empirically.

The device is described in the following text. The figures represent possible exemplary embodiments, which are explained in the following description.

Figure 1:
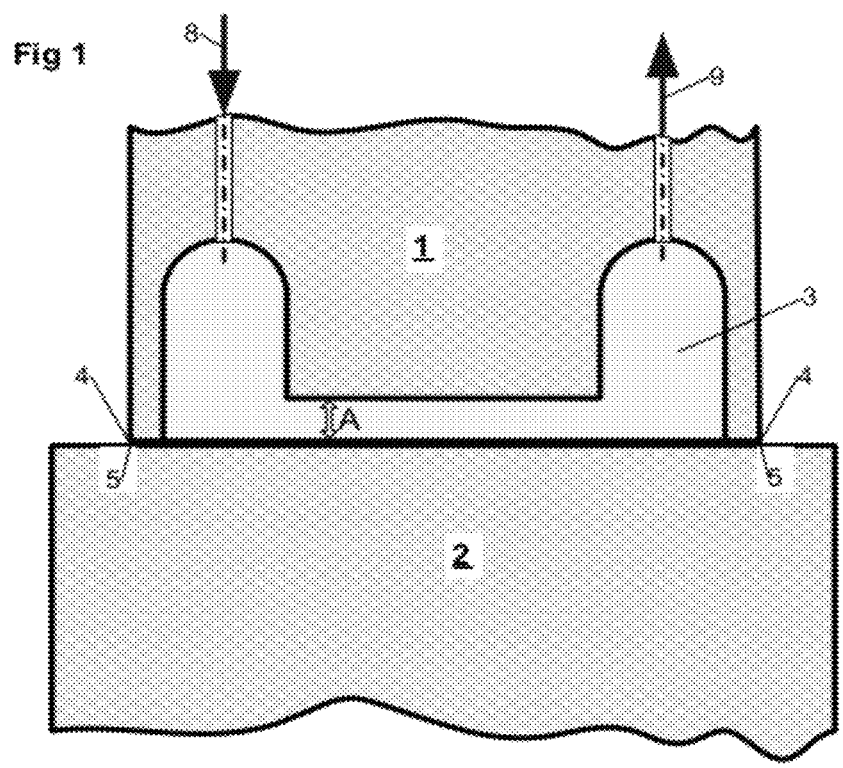
FIG. 1 shows a section through the closed device.

The decisive phase in the above-described method takes place when the device is closed, i.e. when the head 1 of the device forms a unit with the counter head 2 and these stand on one another (FIG. 1). The sealing edge 4 of the head 1 forms a completely closed-off cavity 3 with the counter sealing edge 5 of the counter head 5 and the material of the sample 11, which is clamped between the two sealing edges 4, 5. A liquid, e.g. a rinsing agent, solvent or extracting agent, can be supplied to this cavity 3 via a supply line 8. Material situated in the cavity 3 can leave the latter via the discharge line 9 only. This occurs once the cavity 3 has been filled and liquid is once again introduced via supply line 8. As a result of the provided spatial conditions, the substances mixed into the liquid or dissolved into the latter can be washed out by means of the through-flow or be pressed out through the discharge line 9 in a plug-shaped fashion. So that this occurs as efficiently as possible, the supply line 8 is arranged at one "end" of the cavity 3 and the discharge line 9 is arranged at the other "end". By way of example, if the cavity 3 is cylindrical, the supply line 8 and the discharge line 9 are arranged at the most spaced-apart tangents of the cylinder. The arrangement, which is fixed empirically for the materials to be examined, must be set such that there is as little mixing as possible in the cavity 3, or, should mixing be desired, it should be in a targeted fashion. The described arrangement of supply line 8 and discharge line 9 merely illustrates a possible embodiment. There may also be other variants, such as e.g. a coaxial arrangement with a central supply line and an external discharge line, or else a plurality of supply and/or discharge lines.

Figure 4:
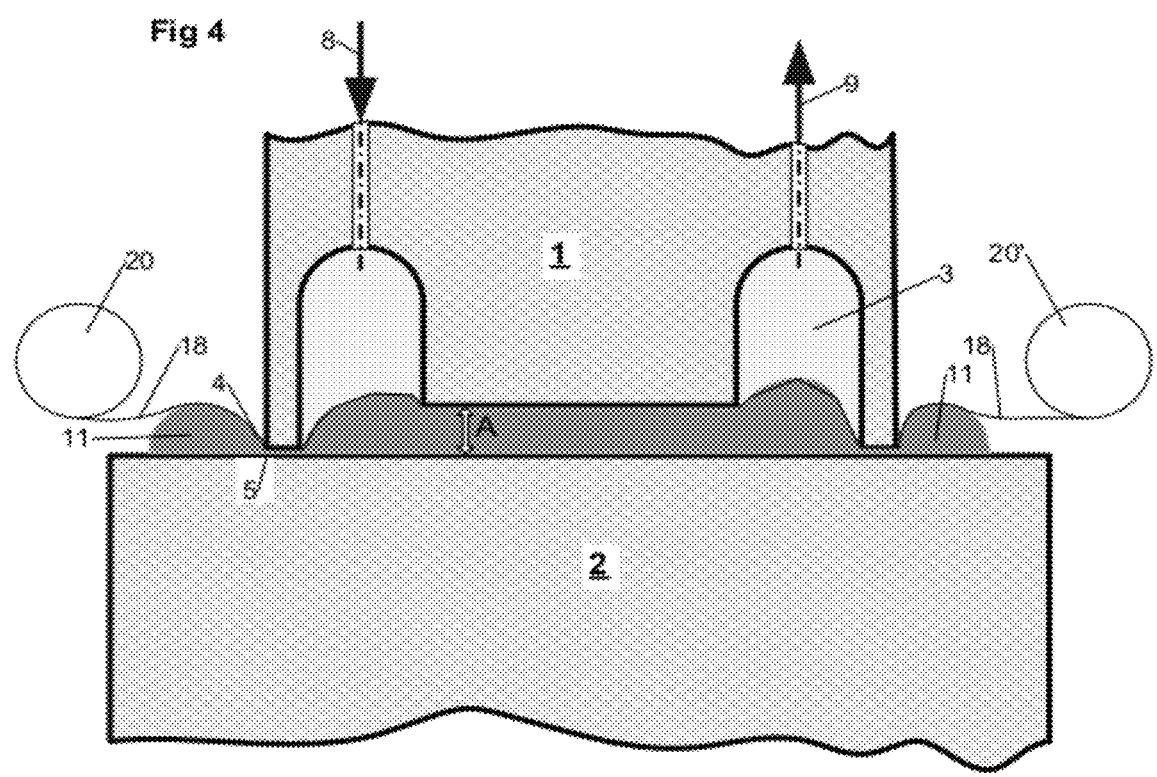
FIG. 4 shows a section through the closed device with a sample and filter cloth.

FIG. 1 illustrates that the sealing edge 4 and the counter sealing edge 5 form a straight line in the illustrated drawing. This is not necessarily the case in practice. The sealing line between sealing edge 4 and counter sealing edge 5 can describe any curve, both in the plan view and spatially. The two sealing edges must seal the cavity 3 uniformly over the whole sealing line in the closed state, i.e. when the head 1 with sealing edge 4 and the counter head 2 with counter sealing edge 5 lie on one another. Although "sealing edges" are discussed here, these can also have a planar design or even be formed with interlocking profiles. Absolute sealing and isolation of the cavity 3 is achieved by virtue of the fact that material of the sample 11 is clamped between sealing edge 4 and counter sealing edge 5 and acts as a "sealant" (FIG. 4). Likewise, a conventional seal, such as e.g. an O-ring with a round or polygonal cross section, can be used as "sealing edge". It may even be advantageous for the shape of the cavity 3, or for individual device solutions described below, if this sealing line has a spatially fitted curve. A further embodiment can also have a conical/convex shape. However, it is by all means feasible for the counter head 2 to constitute a planar surface, on which the sealing edge 4, as illustrated in FIG. 1 in an exemplary fashion, seals a cavity 3.

The device offers the option of matching the method to the samples, substances and carrier liquids. A through-flow, i.e. a washing-out on the surface, can be achieved with an only partly full cavity 3. Likewise, the space may be filled completely in order to avoid e.g. "channeling", which is essential for the above-described soaking process, for solubilizing and for an extraction process.

Figure 2:
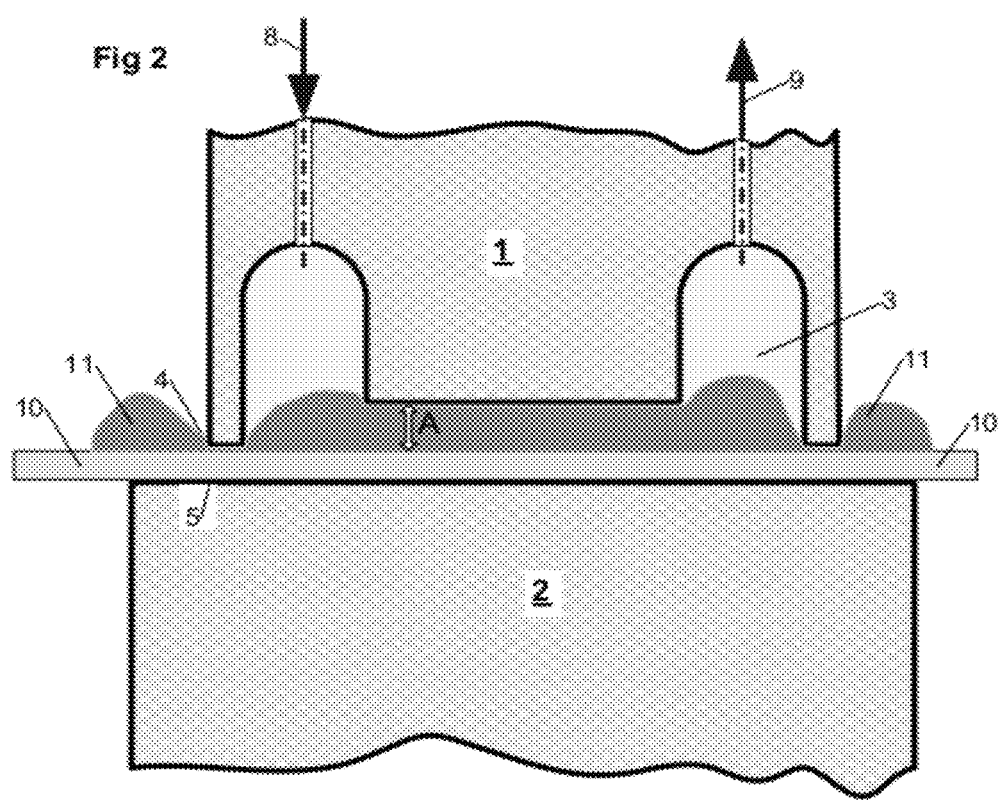
FIG. 2 shows a section through the closed device with a sample on a plate.

Samples 11 in the form of substance stains are often available for examination on ductile or rigid plates 10, wherein the sample is optionally contained in a chromatographic layer applied to the plate. FIG. 2 shows how a sample 11, situated on a plate 10, is introduced into the device between head 1 and counter head 2. The sealing edge 4 delimits the cavity 3 on the thin-layer plate 10, which cavity then contains the substance sample to be dissolved or extracted. Material from the sample 11 and/or the chromatographic layer is also clamped between the sealing edge 4 of the head 1 and the plate 10. In many cases this additionally acts like a sealant and thus helps to seal the cavity 3 in an optimum fashion.

Samples 11 that have a certain amount of inherent rigidity, such as e.g. microscopic sections, can also be inserted directly between head 1 and counter head 2. Substance samples 11 that are applied to an absorbent paper can likewise be processed in precisely this fashion.

Figure 3:
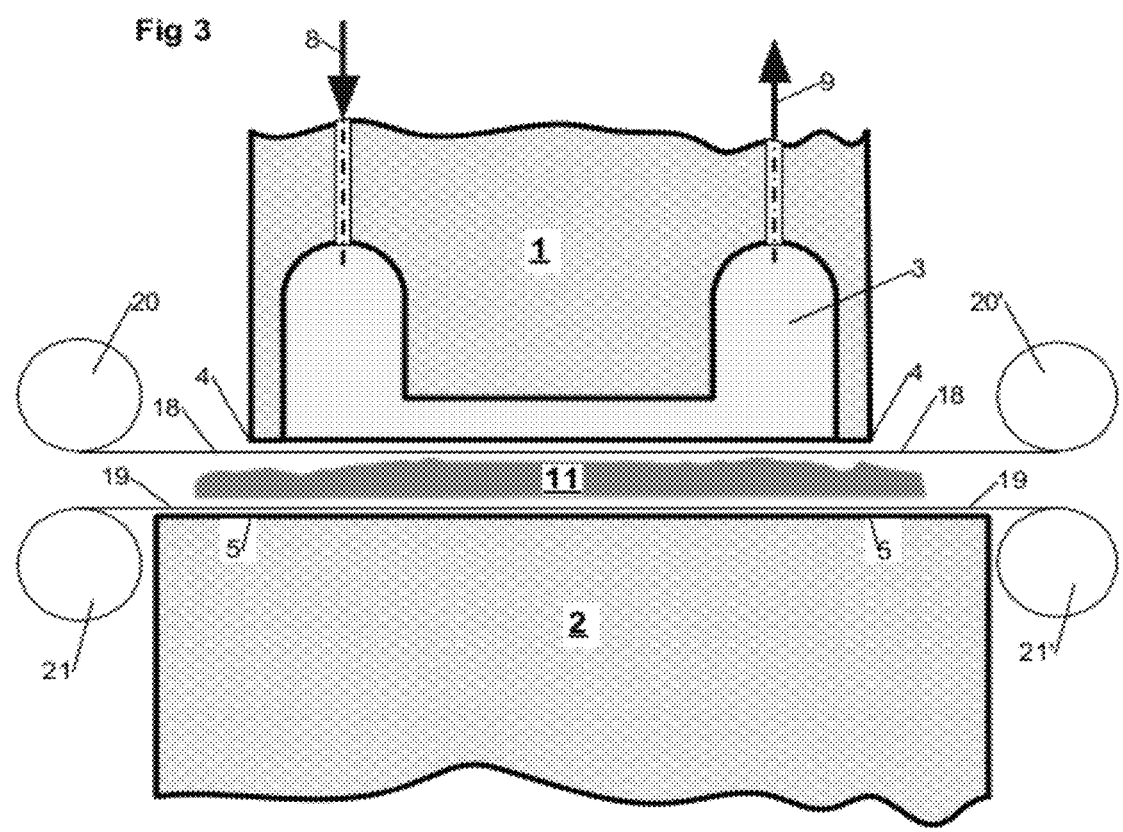
FIG. 3 shows a section through the opened device with a sample and filter cloth and foil cloth.

In the case of devices as per FIG. 1 and FIG. 2, it is usually necessary to install a filter, a so-called "frit", into the discharge line 9. Different filters are required for different samples and substances. A further idea according to the invention is therefore also the application of a filter 18, which is inserted between substance sample 11 and head 1 (FIG. 3). In order to avoid the strenuous insertion of filter 18, it is possible, for example, to select a device which routes the filter 18 under the head 1 from one filter roll 20 through to the filter roll 20'. Then the filter roll 20' is rotated for each new sample 11 such that a new filter 18 comes to rest under the head 1 (FIG. 4). Further forms are also foreseen for the embodiment of the filter 18, such as e.g. individual filter strips, disks or platelets, which together covers one, a plurality of or, in the case of a contiguous arrangement of e.g. one hundred samples 10 on a plate 11, up to more than one hundred samples. In this case, prior to the measurements of all samples, the filter 18 is then brought over the plate 10 with the samples 11 in a manual or, particularly in the case of a small number of samples, automatic fashion.

Depending on requirements, this device can then be used to test a sample 11 that is applied to a plate 10, inherently rigid substance samples such as e.g. microscopic sections or samples 11 situated in absorbent paper, which directly lie on the counter head 2. In this case the filter 18 replaces the "frit" and provides a certain amount of security that the samples 11 are not changed by remains on the head 1 and are thus falsified, because a new, remains-free filter or filter region is used for each new sample.

In order to also achieve this effect on the counter head 2, a second device (FIG. 3) may be applied, which is referred to here as film 19 in the present case. This may but need not be the same filter 18. This film 19 is also routed from one roll 21 to another roll 21 via the counter head 2. Film 19 and/or filter 18 may be treated with a typical "internal standard", such as e.g. an isotope of the active ingredient or other reference substances in a defined amount, so that a calibration measurement of the define isotope is also made, and can be compared, simultaneously with the measurement of the substance.

Figure 6:
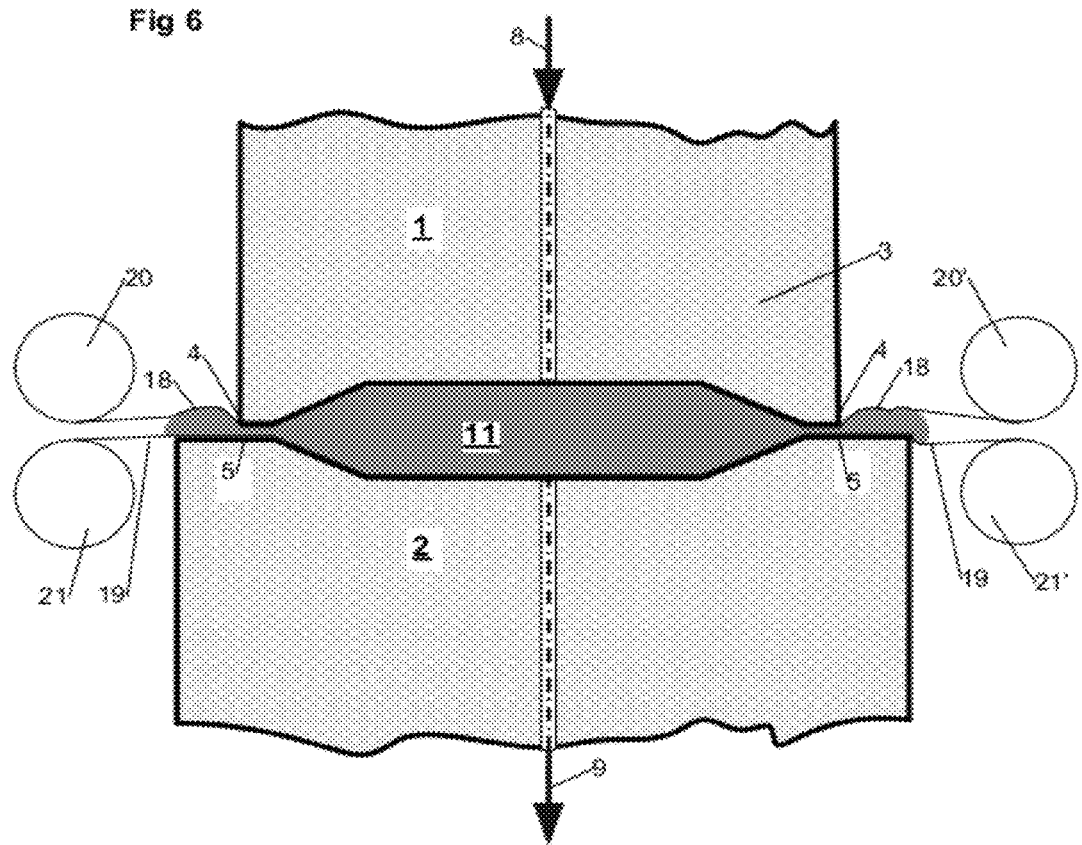
FIG. 6 shows a section through the closed device with a sample and filter cloth and foil cloth for a through-flow.
Figure 7:
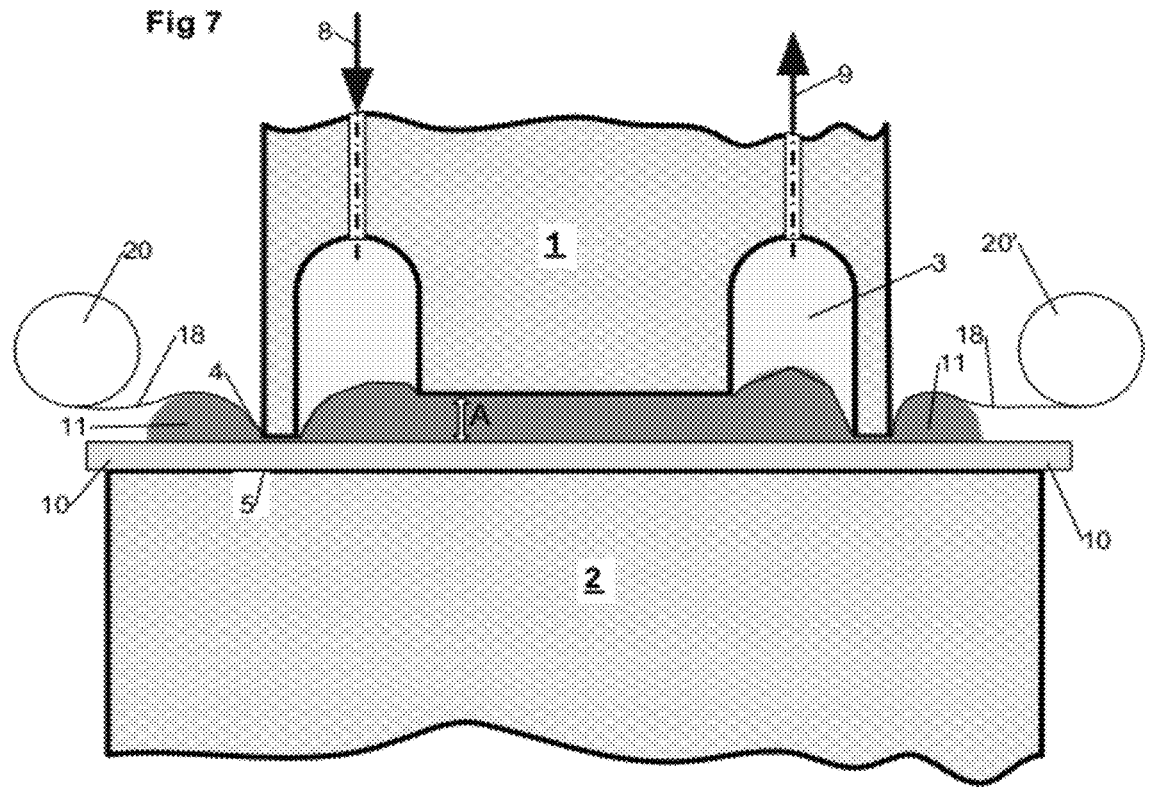
FIG. 7 shows a section through the closed device with a sample on a plate and a filter cloth.
Figure 8:
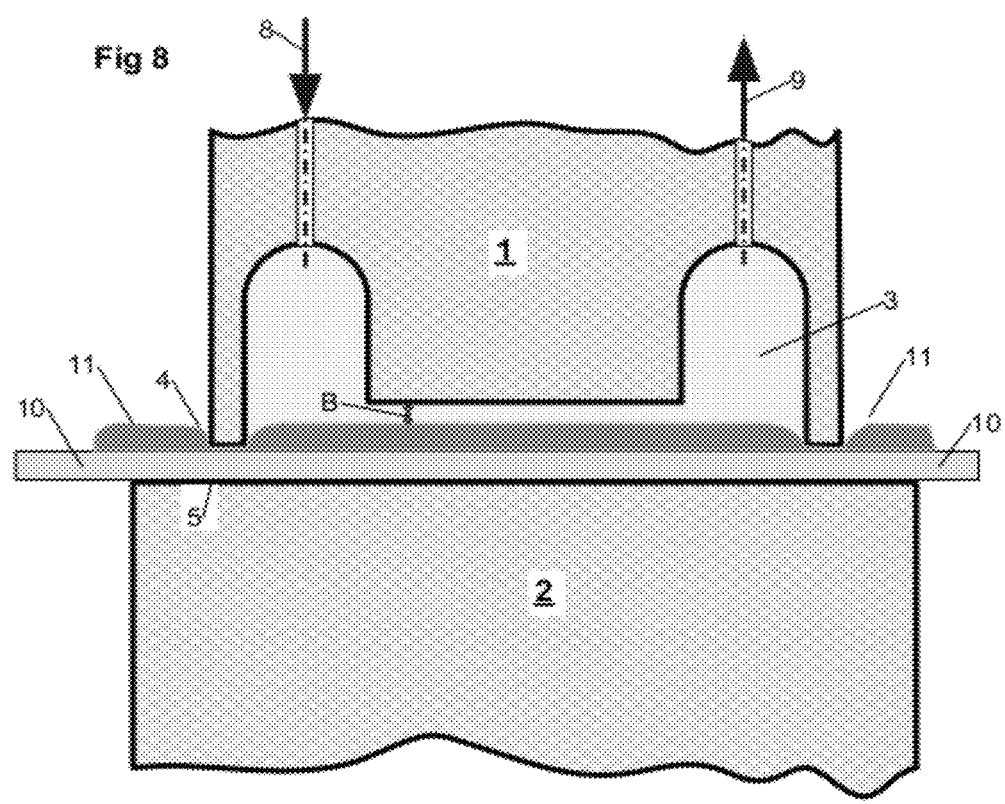
FIG. 8 shows a section through the closed device with a sample on a plate which is submerged.
Figure 9:
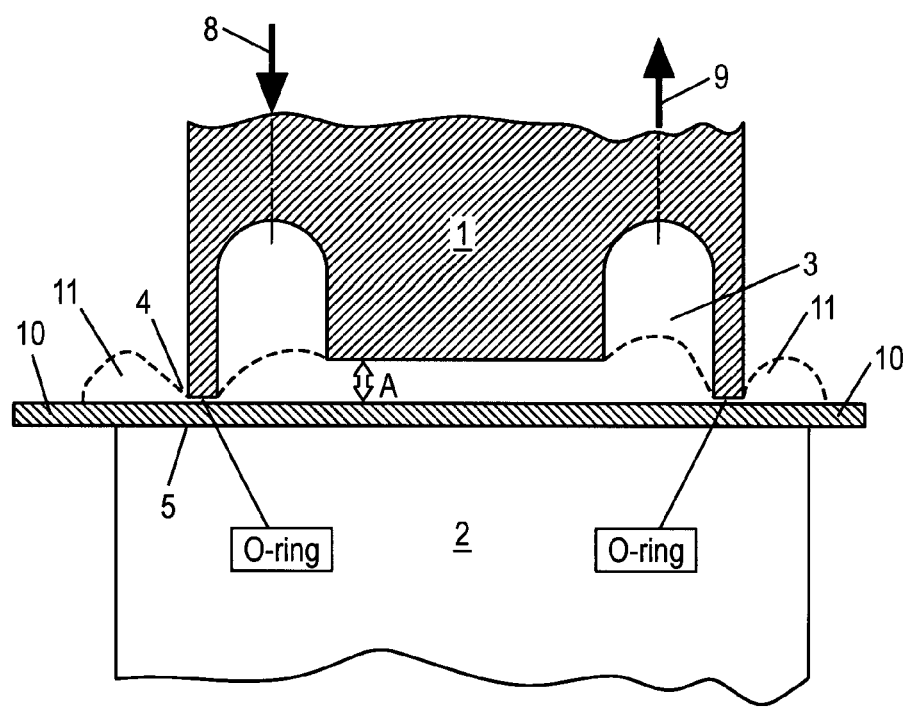
FIG. 9 shows a section through the closed device with a sample on a plate and an O ring formed as a sealing edge.

In the case of the application as per FIG. 3, the film 19 will preferably consist of impermeable material, while a permeable film 19 must be used in the embodiment as per FIG. 6. The filter 18 will consist of a permeable material, is perforated or will be perforated during application in order to be permeable to the liquid. FIG. 3 furthermore shows how, for the processing of each new sample 11, filter 18 can be newly drawn in by means of rolls 20, 20', and film 19 can also be newly drawn in by means of rolls 21, 21'. The filter 18 can furthermore be impregnated by a so-called "internal standard", which is then washed out by the supplied liquid and supplied to the measuring instrument as an additive in the specimen.

If required, both filter 18 and film 19 can assume the function of a ductile or elastic seal. For some samples 10, sealing edge 4 and counter sealing edge 5 can ensure sealing directly or together with filter 18, film 19 and sample 11, either in combination or with one of these. When measuring samples 10 that originate from microscopic sections, it may be expedient to provide the sealing edge 4 and/or the counter sealing edge 5 with a rubber seal, e.g. with a rubber ring with any cross section. It goes without saying that sealing edge 4 and counter sealing edge 5 may also be profile and counter profile, the function of which is similar to a labyrinth seal and which then create the absolute sealing by squished parts of the sample 11.

Figure 5:
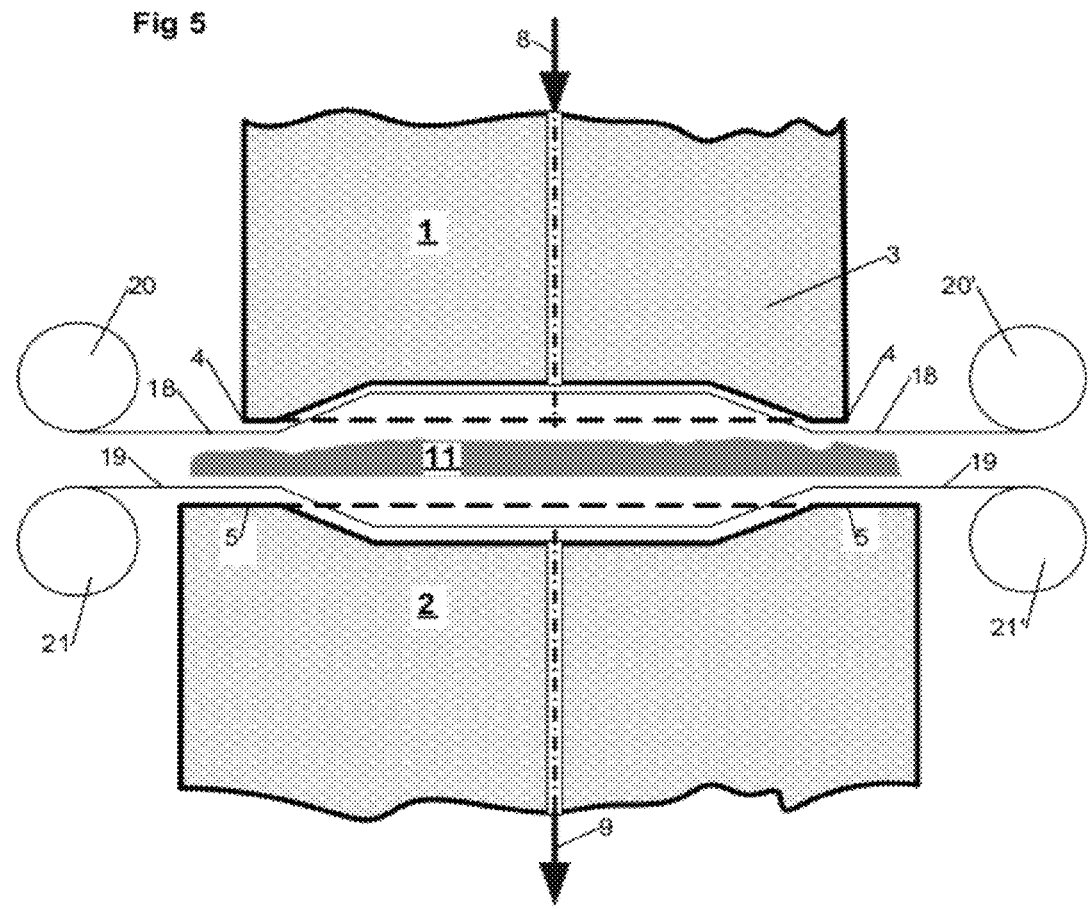
FIG. 5 shows a section through the opened device with a sample and filter cloth and foil cloth for a through-flow.

As shown in FIGS. 5 and 6, an arrangement for the through-flow of the liquid from supply line 8 to the discharge line 9 is also possible. This solution lends itself particularly in the case of samples that have a sufficient inherent rigidity or are applied to neutral filter paper, if the sought-after substance can be eluted by means of washing-out, dissolving or extraction. Although processing is slightly more difficult for samples with lower inherent rigidity, it is not impossible, and so the arrangements illustrated in these drawings and described here also by all means prove their worth in practice.

The invention claimed is:

1. A method for preparing a qualitative and quantitative analysis of a substance, comprising:
   isolating a sample including the substance embedded in a matrix, the matrix consists of insolubly solid or soluble components, in a completely closed-off and sealed cavity by clamping a plate containing the sample between sealing edges of a head and a counter head, said plate arranged between said head and counter head;
   bringing said sample into contact with a liquid supplied by a supply line, wherein said liquid at least partially flows through said sample; and
   supplying at least a portion of the substance, as a specimen, to a measuring instrument via a discharge line.

2. The method as claimed in claim 1, wherein, prior to flowing over and at least partially flowing through, said introduced liquid remains in said cavity together with the sample for 1-60 seconds, wherein said liquid acts on said sample during this time, after which said specimen is supplied to the measuring instrument via discharge line.

3. The method as claimed in claim 1, wherein an internal standard is added to the specimen in said cavity, wherein said specimen and said internal standard are together supplied to the measuring instrument via discharge line.

4. A device for carrying out a method for preparing a qualitative and quantitative analysis of substances, the device comprising:
   a head having a sealing edge;
   a counter head;
   a cavity formed between the head and the counter head, the cavity provided with a supply line and a discharge line;
   a plate containing a substance for analysis, arranged between the head and the counter head, wherein the cavity is surrounded by a separation line formed by the sealing edge of the head and a surface of the plate so that in a closed state the cavity is sealed and isolated from an external atmosphere.

5. The device as claimed in claim 4, wherein said counter head is a planar surface.

6. The device as claimed in claim 4, wherein said supply line and discharge line are arranged on the outer contour of said cavity and are located across from one another on opposite sides of the cavity, the supply line located at one "end" of the cavity and the discharge line arranged at the other "end" of the cavity.

7. The device as claimed in claim 4, wherein said cavity is embodied such that it has a cross section A between said supply line and discharge line.

8. The device as claimed in claim 4, wherein said plate is made of glass, wherein the material of the said sample is clamped between said sealing edge and plate.

9. The device as claimed in claim 4, wherein said plate is a ductile plate, which is slightly penetrated by said sealing edge.

10. The device as claimed in claim 4, wherein said sealing edge is provided with an O-ring.

* * * * *